(12) United States Patent
Lee et al.

(10) Patent No.: US 8,901,620 B2
(45) Date of Patent: Dec. 2, 2014

(54) BIOSENSOR COMPRISING REDUCED GRAPHENE OXIDE LAYER

(75) Inventors: Hyoyoung Lee, Suwon-si (KR); Peng Cui, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 130 days.

(21) Appl. No.: 13/584,318

(22) Filed: Aug. 13, 2012

(65) Prior Publication Data

US 2013/0306934 A1    Nov. 21, 2013

(30) Foreign Application Priority Data

May 16, 2012    (KR) .......................... 10-2012-0052106

(51) Int. Cl.
*G01N 27/403*    (2006.01)

(52) U.S. Cl.
USPC  257/253; 257/12; 257/E51.025; 257/E51.38; 438/49; 977/753; 977/958

(58) Field of Classification Search
None
See application file for complete search history.

(56) References Cited

FOREIGN PATENT DOCUMENTS

KR    10-2011-0121569 A    11/2011

OTHER PUBLICATIONS

Cui, Peng, et al., "Nonvolatile Memory Device Using Gold Nanoparticles Covalently Bound to Reduced Graphene Oxide," ACSNANO, Aug. 15, 2011, pp. 6826-6833, vol. 5, No. 9.

*Primary Examiner* — Yasser A Abdelaziez
(74) *Attorney, Agent, or Firm* — NSIP Law (57) ABSTRACT

The present invention relates to a horizontal biosensor, comprising a reduced graphene oxide layer formed on a substrate; a molecular linker formed on the reduced graphene oxide layer; and a metal nanoparticle layer formed on the molecular linker.

7 Claims, 13 Drawing Sheets

FORMING A REDUCED GRAPHENE OXIDE LAYER ON A SUBSTRATE

FORMING A MOLECULAR LINKER ON THE REDUCED GRAPHENE OXIDE LAYER

FORMING A METAL NANOPARTICLE LAYER ON THE MOLECULAR LINKER

HORIZONTAL BIOSENSOR

BIOSENSOR COMPRISING REDUCED GRAPHENE OXIDE LAYER

CROSS-REFERENCE TO RELATED APPLICATION

This application claims the benefit of Korean Patent Application No. 10-2012-0052106 filed May 16, 2012, the entire disclosures of which are incorporated herein by reference.

FIELD OF THE INVENTION

The present disclosure relates to a horizontal biosensor using a reduced graphene oxide.

BACKGROUND OF THE INVENTION

Graphene is electrically, mechanically, and chemically stable and outstanding, and also, the graphene is an excellent conductor capable of moving electrons about 100 times faster than silicon and carrying about 100 times more electric current than copper. Thus, a lot of research on production and application of graphene has been carried out. By way of example, Korean Patent Application No. 10-2011-0040229 describes "Graphene thin film by electrostatic spraying deposition and manufacturing method thereof". However, for the present, a method for controllable mass production of graphene needs to be developed, and also, a problem of low production yield and high cost needs to solved.

Recently, in order to solve problems incurred when graphene is mass-produced by conventional methods, there has been developed a method for producing a chemically reduced graphene oxide (hereinafter, referred to as "rGO") having a semiconducting property. By way of example, there has been developed a method in which oxidized graphite is produced to a graphene oxide (hereinafter, referred to as "GO") nano-sheet and the GO is reduced to produce an rGO of high quality.

An rGO thin film including a monolayer or double layers has a semiconducting property, and an rGO film thicker than the rGO thin film has a semimetallic property. Further, the rGO thin film has a low sheet resistance and a high transparency. An rGO thin film can be used for improving sensitivity within a biosensor due to its semiconducting property.

A biosensor has been used in various fields of industry. In order to improve performance of the biosensor, it is necessary to use a sensitive element having a high sensitivity. By way of example, there is a research in which a gold nanoparticle (hereinafter, referred to as "AuNP") physically included in an organic layer or physically attached onto the organic layer is used as a sensitive element in order to improve sensitivity of a biosensor.

However, if the AuNP is physically included in the organic layer or attached onto the organic layer, it is difficult to uniformly disperse the AuNP in the organic layer and a life span of the biosensor can be reduced. Further, it is difficult to find out whether "charging effect" directly related to performance as a sensitive element can be shown due to presence of the AuNP, presence of the organic layer, or presence of both the AuNP and the organic layer, and, thus, it is difficult to make a technical improvement.

DISCLOSURE OF THE INVENTION

Problems to be Solved by the Invention

The present inventors found that in case of using a biosensor including, as a sensitive element, a reduced graphene oxide (rGO) layer and a metal nanoparticle layer which are chemically bonded by a molecular linker, for example, a hybrid layer including a gold nanoparticle (AuNP) layer, problems of a conventional biosensor can be solved and accomplished the present disclosure.

In view of the foregoing, the present disclosure provides a horizontal biosensor including the hybrid layer and a preparing method thereof.

However, the problems sought to be solved by the present disclosure are not limited to the above description and other problems can be clearly understood by those skilled in the art from the following description.

Means for Solving the Problems

In accordance with a first aspect of the present disclosure, there is provided a horizontal biosensor, including a reduced graphene oxide layer formed on a substrate; a molecular linker formed on the reduced graphene oxide layer; and a metal nanoparticle layer formed on the molecular linker.

In accordance with a second aspect of the present disclosure, there is provided a method for preparing a horizontal biosensor, and the method includes forming a reduced graphene oxide layer on a substrate; forming a molecular linker on the reduced graphene oxide layer; and forming a metal nanoparticle layer on the molecular linker.

Effect of the Invention

A horizontal biosensor including a hybrid layer prepared in accordance with the present disclosure has a charging effect superior to a conventional biosensor and has a high sensitivity.

Further, a preparing method of the horizontal biosensor in accordance with the present disclosure includes coating a graphene oxide (GO) by means of a spin coating method or a spin casting method which is a simple and low-cost method and acquiring a rGO by simply reducing the GO with a reducing agent such as hydrazine or HI. Thus, this method is equally or more economical as compared with a conventional method and can be highly commercialized.

Furthermore, the horizontal biosensor in accordance with the present disclosure uses a partially modified semiconductive rGO as a supporter of a metal nanoparticle, for example, a gold nanoparticle (AuNP), showing a charging effect. The rGO is a semiconducting material having a high sensitivity. The rGO has an excellent hole and electron mobility, and it is thus advantageous as a matrix for activating a function. Further, the rGO provides a covalent bonding site, and it thus becomes easy to array a monolayer of a metal nanoparticle such as AuNP.

Moreover, the horizontal biosensor in accordance with the present disclosure uses chemical bonding between the rGO and the AuNP with a molecular linker instead of physical bonding used in a conventional method. There has been known that graphene such as the rGO and the AuNP do not have chemical reactivity, and, thus, chemical bonding therebetween has not been conventionally tried. However, in accordance with the present disclosure, it is possible to simply make a chemical bonding by using a molecular linker of which both ends are partially modified.

Furthermore, the horizontal biosensor in accordance with the present disclosure provides more clear explanation of a cause of "charging effect" directly related to performance as a sensitive element, and it is thus possible to make a technical improvement in future.

DETAILED DESCRIPTION FOR CARRYING OUT THE INVENTION

Hereinafter, illustrative embodiments and examples will be described in detail so that inventive concept may be readily implemented by those skilled in the art. However, it is to be noted that the present disclosure is not limited to the illustrative embodiments and examples but can be realized in various other ways. In drawings, parts irrelevant to the description are omitted for the simplicity of explanation, and like reference numerals denote like parts through the whole document.

Through the whole document, the term "connected to" that is used to designate a connection of one element to another element includes both a case that an element is "directly connected to" another element and a case that an element is "electronically connected to" another element via still another element.

Through the whole document, the term "on" that is used to designate a position of one element with respect to another element includes both a case that the one element is adjacent to the another element and a case that any other element exists between these two elements.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise. The term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from the group consisting of components, steps, operation and/or elements described in Markush type and thereby means that the disclosure includes one or more components, steps, operations and/or elements selected from the Markush group.

Through the whole document, the term "graphene" is a polycyclic aromatic molecule formed by covalently bonding multiple carbon atoms. The covalently bonded carbon atoms form a six-member carbon ring as a repeating unit and may further includes a five-member carbon ring and/or a seven-member carbon ring. Therefore, a sheet made of the graphene can be seen as, but not limited to, a monolayer of covalently bonded carbon atoms. The sheet made of the graphene may have various structures depending on a content of the five-member carbon ring and/or the seven-member carbon ring which may be included in the graphene. If a sheet made of the graphene is configured as a monolayer, multiple sheets may be stacked to form multiple layers. A side end of the graphene sheet may be saturated with, but not limited to, a hydrogen atom.

Through the whole document, the term "horizontal biosensor" is a biosensor including a source electrode and a drain electrode existing on the same plane and including a layered hybrid layer of a reduced graphene oxide layer-a molecular linker-a gold nanoparticle layer between the source electrode and the drain electrode. A structure thereof can be understood with reference to, but not limited to, claim 1 or FIGS. 1 and 2 of the present disclosure.

Hereinafter, illustrative embodiments and examples will be explained in detail with reference to the accompanying drawings.

In accordance with a first aspect of the present disclosure, there is provided a horizontal biosensor 50 including a reduced graphene oxide (rGO) layer 20 formed on a substrate 10, a molecular linker 30 formed on the reduced graphene oxide layer 20, and a metal nanoparticle layer 40 formed on the molecular linker 30.

In accordance with the first aspect of the present disclosure, a hybrid layer 60 of "the reduced graphene oxide (rGO) layer 20 formed on the substrate 10, the molecular linker 30 formed on the reduced graphene oxide layer 20, and the metal nanoparticle layer 40 formed on the molecular linker 30" included in the horizontal biosensor 50, can be abbreviated to "rGO-molecular linker-AuNP" or "AuNP-frGO (meaning a rGO modified by a molecular linker; functionalized rGO)" if the metal nanoparticle is a gold nanoparticle (AuNP). Therefore, hereinafter, if necessary, the hybrid layer 60 will be described as "AuNP-frGO" which should be understood as the hybrid layer 60.

Regarding the first aspect of the present disclosure, "biosensor" is a sensor for detecting presence of a bio material. The biosensor identifies a kind of a material by bonding a target material and a probe material. The target material is a target object to be sensed, and the probe material is a material capable of being specifically and selectively bonded to the target material. The biosensor may have various detection methods. By way of example, an electrochemical biosensor, an optical biosensor, and the like may be used.

The optical biosensor is capable of detecting whether or not a target material is bonded with an optical microscope without a specific electrical device, and thus, it is relatively simple and economical. However, there is a problem that the optical biosensor requires a specific dye for sensing an optical characteristic change caused by bonding between materials, a target material or a probe material needs to be labeled with the dye. Further, the dye which is difficult to synthesize is costly, and thus, economically, it is not desirable. Therefore, in accordance with the first aspect of the present disclosure, there is provided a biosensor that electrochemically senses a target material.

A biosensor has been developed with an emphasis on improvement in sensitivity by an electrode surface treatment. However, a biosensor used for several diseases such as cancer may be required to detect a monomolecular material. Accordingly, in order to develop a biosensor capable of accurately diagnosing various diseases, micro concentration detectability and reproducibility are no less important than a high sensitivity. Therefore, in accordance with the first aspect of the present disclosure, there is provided a biosensor having micro concentration detectability and reproducibility as well as a high sensitivity.

Further, regarding a sensitivity of a biosensor, the amount of a bio material immobilized on an electrode surface is an important factor affecting the sensitivity of the biosensor. Thus, an effective area where the bio material can be immobilized can be an important factor affecting development of a high-sensitivity biosensor. Therefore, in accordance with the first aspect of the present disclosure, there is provided a biosensor having an increased electrode effective area directly related to improvement in a sensitivity of a sensor.

In this regard, graphene and a metal nanoparticle included in the biosensor in accordance with the first aspect of the present disclosure are important elements in relation to performance of the biosensor. First, the graphene is a material which is flexible and has a very high electrical conductivity and a great surface area, and thus, it is suitable for an element of the biosensor. However, a surface treatment for the graphene is complicated and limited, and thus, it is difficult to use the graphene as a single element of the biosensor. Therefore, in accordance with the present disclosure, the metal nanoparticle is chemically bonded to a surface of the graphene with a molecular linker. Typically, a metal film tends to modify bio materials and may lower activity thereof, and, thus, it has not been known to be suitable for a biosensor. However, the metal nanoparticle such as a gold nanoparticle of the present disclosure prevents modification of an adsorbed bio material. Therefore, while a great amount of a bio material is immortalized on a surface of the gold nanoparticle by means of adsorption, it is possible to prevent modification of the bio material. Further, the gold nanoparticle maximizes an electrode area and also maximizes transfer of electrons generated by a chemical reaction.

By way of example, the metal nanoparticle included in the biosensor in accordance with the first aspect of the present disclosure may be, but is not limited to, a gold nanoparticle (AuNP), a platinum nanoparticle, or palladium nanoparticle, and may include various metal nanoparticles capable of maximizing an electrode area and maximizing transfer of electrons generated by a chemical reaction.

As described above, the biosensor in accordance with the first aspect of the present disclosure includes a graphene layer and a metal nanoparticle layer, and thus, it is possible to improve sensitivity for a detection target material. By way of example, recently there has been developed an electrochemical biosensor that uses an enzyme and detects an electric signal generated by an electrochemical reaction between the enzyme and a substrate.

If the biosensor in accordance with the first aspect of the present disclosure is applied to the biosensor using the enzyme, it is possible to maximize activity of the enzyme that reacts with a detection target material. Herein, the metal nanoparticle of the biosensor allows the enzyme to be immobilized stably, and the graphene increases a transfer rate of electrons generated as products of an enzyme reaction, but the present disclosure is not limited thereto.

Hereinafter, respective components of the biosensor in accordance with the first aspect of the present disclosure will be explained in detail, but the present disclosure is not limited thereto.

By way of example, the substrate 10 of the biosensor in accordance with the first aspect of the present disclosure may include, but is not limited to, a source electrode 12 and a drain electrode 14. Further, by way of example, the substrate 10 may include, but is not limited to, a microfluidic channel.

By way of example, if the substrate 10 includes but the source electrode 12 and the drain electrode 14, each of the source electrode 12 and the drain electrode 14 may include, but is not limited to, a metal electrode or an organic electrode. The metal electrode may include, for example, but not limited to, a gold (Au) electrode. By way example, the substrate 10 may be, but is not limited to, a $SiO_2$ substrate. The $SiO_2$ substrate may be patterned in advance such that the Au source electrode 12 and the Au drain electrode 14 exist on the same plane with space between them, but the present disclosure is not limited thereto.

In accordance with an illustrative embodiment of the present disclosure, the reduced graphene oxide (rGO) layer 20 may be a thin layer including at least, but not limited to, one layer, and thus may have a semiconducting property. By way of example, the reduced graphene oxide (rGO) layer 20 may be a thin layer including, but not limited to, from about 1 layer to about 2 layers, from about 1 layer to about 10 layers, from about 1 layer to about 20 layers, from about 1 layer to about 30 layers, from about 1 layer to about 40 layers, from about 1 layer to about 50 layers, from about 1 layer to about 80 layers, from about 1 layer to about 100 layers, from about 20 layers to about 30 layers, from about 20 layers to about 40 layers, from about 20 layers to about 50 layers, from about 20 layers to about 80 layers, from about 20 layers to about 100 layers, or from about 50 layers to about 100 layers, and thus may have a semiconducting property. By way of example, the rGO may be formed in a thin film instead of a thick film in order to have a semiconducting property instead of a semi-metallic property, but the present disclosure is not limited thereto. Further, the reduced graphene oxide (rGO) layer 20 may be formed by, but not limited to, forming a graphene oxide layer on the substrate 10 and then reducing the graphene oxide layer. In this case, in order to reduce the graphene oxide layer, a reducing agent, for example, but not limited to, hydrazine or HI may be used.

In accordance with an illustrative embodiment of the present disclosure, the molecular linker 30 may include, but is not limited to, a diazonium group at its first end, and a thiol group (—SH), a hydroxyl group (—OH), or an amine group (—$NH_2$) at its second end. By way of example, the molecular linker 30 may include, but is not limited to, 4-mercapto-benzenediazonium tetrafluoroborate (hereinafter, referred to as "MBDT") as a bifunctional molecular linker 30 of which both ends are partially modified such that a diazonium group is included at its first end and a thiol group is included at its second end. By way of example, the molecular linker 30 may include, but is not limited to, a p-conjugated molecular linker 30 used to chemically bond each of the rGO and the AuNP. By way of example, but not limited to, a phenyl group as the most simple p-conjugated aromatic functional group may be selected as a wire for conjugation.

In accordance with an illustrative embodiment of the present disclosure, the diazonium group at the first end of the molecular linker 30 may be immobilized on the reduced graphene oxide (rGO) layer 20 by using a self-assembly function, but the present disclosure is not limited thereto.

In accordance with an illustrative embodiment of the present disclosure, the thiol group, the hydroxyl group, or the amine group at the second end of the molecular linker 30 may be covalently bonded to the metal nanoparticle layer, for example, the gold nanoparticle (AuNP) layer 40, but the present disclosure is not limited thereto. By way of example, if a functional group at the second end of the molecular linker 30 is a thiol group and the metal nanoparticle layer is a gold nanoparticle (AuNP) layer, a covalent bond between the thiol group and the AuNP may be formed spontaneously, but the present disclosure is not limited thereto. Due to the thiol group at the second end of the molecular linker 30, monolayered AuNP operating as a capacitor may be formed, but the present disclosure is not limited thereto. The covalent bond can be confirmed by an XPS analysis.

By way of example, the molecular linker 30 between the rGO and the AuNP in the AuNP-frGO hybrid layer 60 may provide an energy barrier, and thus, charge transfer of the AuNP can be maintained for some time, resulting in a non-linear current-voltage (I-V) hysteresis loop and a long retention time, but the present disclosure is not limited thereto.

In this regard, it is generally known that a charged state of AuNP may lead to a space-charge field that can prevent or accelerate electron transfer. The AuNP operating as the capacitor may be a charged mobile carrier or a discharged mobile carrier depending on a bias voltage applied between the source electrode 12 and the drain electrode 14 included in the biosensor. If the molecular linker 30 is used between the rGO and the AuNP in accordance with the first aspect of the present disclosure, a higher energy barrier may be expected to be provided as compared with a case where AuNP is in direct contact with an organic layer in accordance with a conventional method. The high energy barrier may be caused by, but not limited to, a great difference in potential energy between a lowest unoccupied molecular orbital (LUMO) level of the rGO and a work function of the AuNP. Due to the high energy barrier between the AuNP and the rGO, when a bias voltage is applied to the biosensor including the AuNP-frGO hybrid layer 60 of the present disclosure, the AuNP can access the electrons, causing the electrons to become trapped inside the AuNP. Consequently, these trapped electrons can remain within the AuNP for a long time even after the applied bias is removed, resulting in remarkable performance of the biosensor, but the present disclosure is not limited thereto.

By way of example, in the AuNP-frGO hybrid layer 60 included in the horizontal biosensor 50 in accordance with the first aspect of the present disclosure, monolayered or bilayered semiconducting rGO may serve as a semiconducting mobile channel for charge transfer between the source electrode 12 and the drain electrode 14. The rGO may exist in the form of frGO (functionalized rGO) modified by the bifunctional molecular linker 30, and thus, it becomes easy to form an AuNP monolayer, and the rGO has sufficient sensitivity to detect attachment/detachment of charges to/from the AuNP monolayer, but the present disclosure is not limited there to.

In the horizontal biosensor 50 in accordance with the first aspect of the present disclosure, "charging effect" affecting a sensitivity of the biosensor can be shown due to the AuNP covalently bonded to the frGO, which can be confirmed through a control experiment, but the present disclosure is not limited there to. The control experiment may be carried out by using, but not limited to, a biosensor including only frGO chemically functionalized with the molecular linker 30 without AuNP, or a biosensor in which only AuNP is physically immobilized on rGO without the molecular linker 30.

In accordance with a second aspect of the present disclosure, there is provided a method for preparing the horizontal biosensor 50, and the method includes forming the reduced graphene oxide (rGO) layer 20 on the substrate 10, forming the molecular linker 30 on the reduced graphene oxide layer 20, and forming the metal nanoparticle layer 40 on the molecular linker 30.

By way of example, the substrate 10 may include, but is not limited to, the source electrode 12 and the drain electrode 14.

In accordance with an illustrative embodiment of the present disclosure, the forming the reduced graphene oxide (rGO) layer 20 may include, but is not limited to, forming a graphene oxide (GO) layer on the substrate 10 and reducing the graphene oxide layer.

By way of example, the forming the reduced graphene oxide (rGO) layer 20 may include, but is not limited to, forming a graphene oxide (GO) layer on the substrate 10 by means of a spin casting method, and reducing the graphene oxide layer with hydrazine or HI (hydrogen iodide). By using a simple and economical method, for example, but not limited to, a conventional spin casting method in order to form the GO, it is possible to improve economic feasibility and possibility of commercialization of the biosensor in accordance with the present disclosure.

The forming the graphene oxide (GO) layer on the substrate 10 may be carried out by using various methods including, for example, but not limited to, a drop casting method, a spin casting method, or a Langmuir Blogett method.

Reducing the graphene oxide (GO) layer may be carried out by using various reducing agents including, for example, but not limited to, hydrazine or HI.

Figure 1:
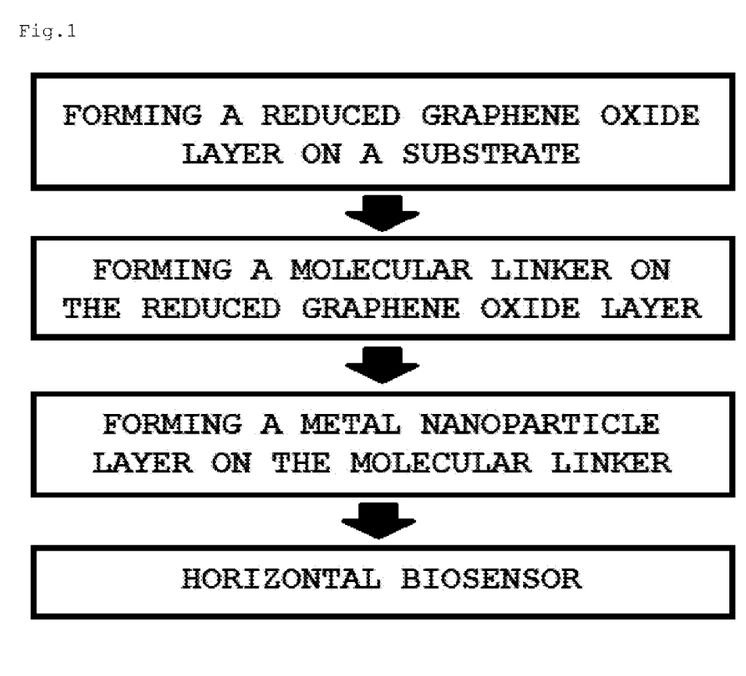
FIG. 1 is a flow chart showing a sequential process for preparing a horizontal biosensor in accordance with an illustrative embodiment of the present disclosure.
Figure 2:
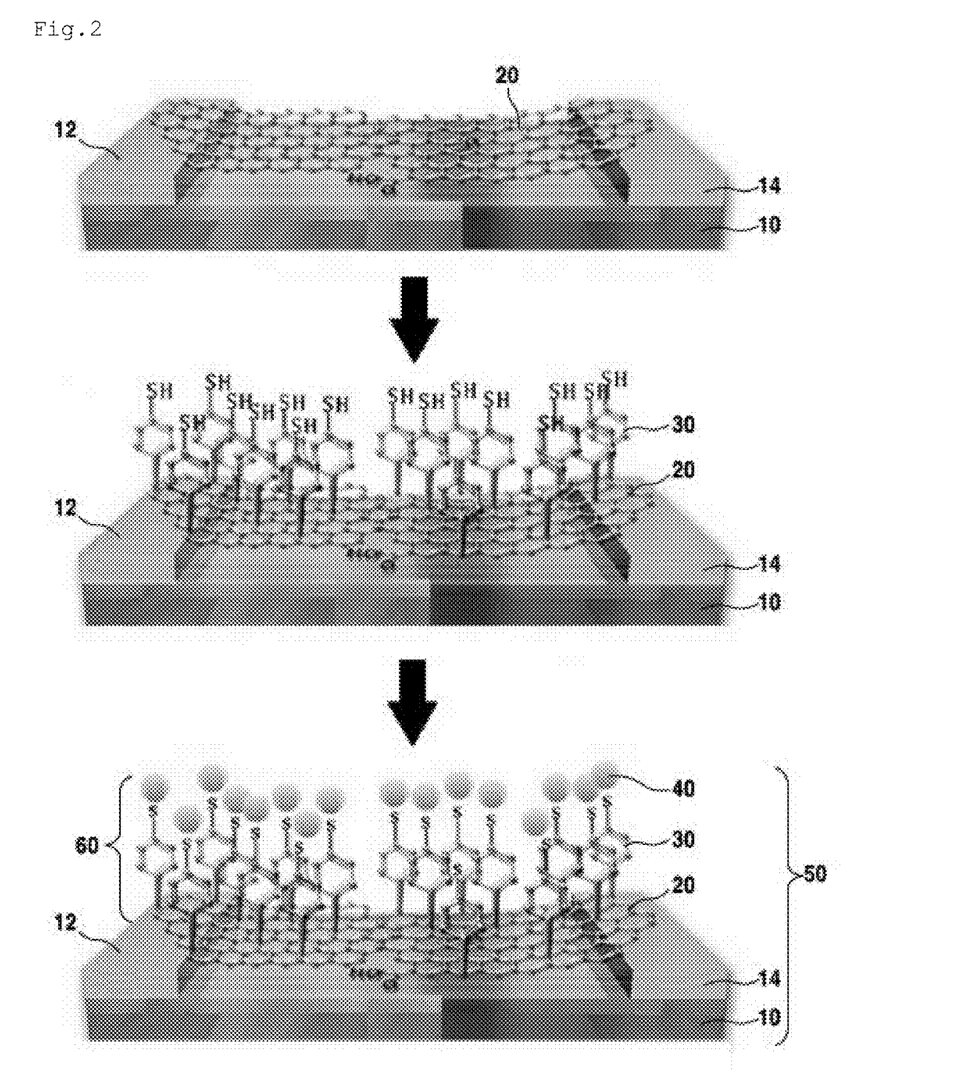
FIG. 2 is a schematic diagram illustrating a process for preparing a horizontal biosensor in accordance with an illustrative embodiment of the present disclosure.

Regarding the method for preparing the horizontal biosensor 50 in accordance with the second aspect of the present disclosure, FIG. 1 is a flow chart showing a sequential process for preparing a horizontal device including the AuNP-frGO hybrid layer 60, and FIG. 2 is a schematic diagram illustrating a process for preparing a horizontal device including the AuNP-frGO hybrid layer 60 in accordance with an illustrative embodiment of the present disclosure.

By way of example, in a first step of FIG. 2, monolayered or bilayered GO may be formed on the pre-patterned substrate 10 including the source electrode 12 and the drain electrode 14 by means of, but not limited to, a spin casting method. The GO may be prepared by a publicly known conventional method. The GO may be dispersed uniformly in distilled water and may be used in the spin casting method, but the present disclosure is not limited thereto. Then, the GO may be chemically reduced by using, but not limited to, hydrazine steam, so that rGO can be obtained.

In a second step of FIG. 2, the rGO may be functionalized by using the molecular linker 30 containing the thiol group by means of a self-assembly technique, and thus the frGO can be formed, but the present disclosure is not limited thereto. The frGO may contain, but is not limited to, a surface of the thiol group under the influence of the molecular linker 30.

By way of example, in a third step of FIG. 2, the AuNP may be spontaneously immobilized on the surface of the thiol group of the frGO, so that the horizontal biosensor 50 including the AuNP-frGO hybrid layer 60 can be prepared, but the present disclosure is not limited thereto.

Hereinafter, examples regarding the horizontal biosensor in accordance with the present disclosure will be explained in detail, but the illustrative embodiments are not limited thereto.

EXAMPLES

1. Synthesis of MBDT Salt

In the present example, in order to synthesize a MBDT salt used as a molecular linker, first, 4-aminothiophenol was dissolved in ethanol in a flask, and a 48% aqueous fluoroboric acid solution was added to the flask, and thus, a mixture was formed. The resultant mixture was then cooled to about −5° C. Then, isoamyl nitrite was added dropwise to the mixture, and then the mixture was stirred for about 0.5 hours. Then, the mixture was diluted with diethyl ether, and a precipitate of MBDT was formed as brown crystals. Then, the precipitate of MBDT was purified by recrystallization using acetone and cold diethyl ether, respectively.

2. Preparation of GO Solution.

In the present example, graphene oxide (GO) was synthesized using a modified Hummer's method. To be specific, the GO of about 40 mg and distilled water of about mL were mixed together in a falcon-tube. Herein, to disperse the GO in the distilled water, if necessary, sonication for more than about 2 hours was performed, and a Branson ultrasonicator was used. The prepared GO solution was shaken at about 200 rpm for about 1 hour, centrifuged at about 500 rpm for about 1.5 hours, and then left standing for about 2 hours. Then, a supernatant was separated and stored until needed for further experimentation. Before use, the supernatant of the GO solution was sonicated for about 1 hour, shaken at about 200 rpm for about 1 hour, and left standing for about 2 hours.

3. Preparation of Horizontal Biosensor

In order to prepare a horizontal biosensor, a $SiO_2$ substrate including an Au source electrode and an Au drain electrode was prepared, and the $SiO_2$ substrate was chemically cleaned using a piranha solution, which needs to be handled with care, as a mixture of hydrogen peroxide and sulfuric acid. The $SiO_2$ substrate was then washed with diluted water several times. Then, by using a microsyringe, the prepared GO solution was spin-coated onto the substrate at about 4000 rpm. The substrate spin-coated with the GO solution was dried for about 24 hours in a vacuum. Then, the substrate spin-coated with the GO solution was placed on the top of inner space of a glass chamber, and hydrazine monohydrate was dropped into the chamber. After sealing the chamber, the whole system was heated at about 80° C. for about 24 hours, and the hydrazine was vaporized to reduce GO into rGO.

After the rGO was formed by the reduction, a MBDT solution in acetonitrile (ACN) was prepared at a concentration of about 70 mM. Then, the substrate including the rGO was immersed in the MBDT solution for about 24 hours, so that the substrate including frGO functionalized with the MBDT was formed. The present step was performed in a glove box. The substrate including the frGO was washed thoroughly with ACN and acetone, and blown with a nitrogen gas to remove the solvent. The substrate including the frGO was kept in a vacuum before the next step was performed.

Then, for immobilization of AuNP on the substrate including the frGO, the substrate including the frGO was placed into an Au colloid solution for about 120 hours, and then washed with diluted water, and blown dry with a nitrogen gas.

The horizontal biosensor including an AuNP-frGO hybrid layer prepared after the above-described steps was then kept in a vacuum before it was used for property tests.

4. Design for Surface and Electrical Property Test

In order to check a surface property of the AuNP-frGO hybrid layer included in the horizontal biosensor prepared in the present example, AFM and Raman spectrum were used. In that case, an atomic force microscopy (SPA 3800, Seiko) and a Raman spectroscopy (Reinshaw, RM1000-In Via) were used.

Further, in order to check an electrical property of the AuNP-frGO hybrid layer included in each of the horizontal biosensor prepared in the present example, a 4200 Keithley semiconductor characterization system was used.

5. Result of Surface and Electrical Property Test

In the present example, in order to check a chemical property and a surface property of the AuNP-frGO hybrid layer included in the horizontal biosensor, XPS, Raman spectrum, and AFM were used. Results thereof are shown in FIGS. 3a to 3f, FIG. 4, and FIGS. 5a to 5c, respectively.

Figure 3A:
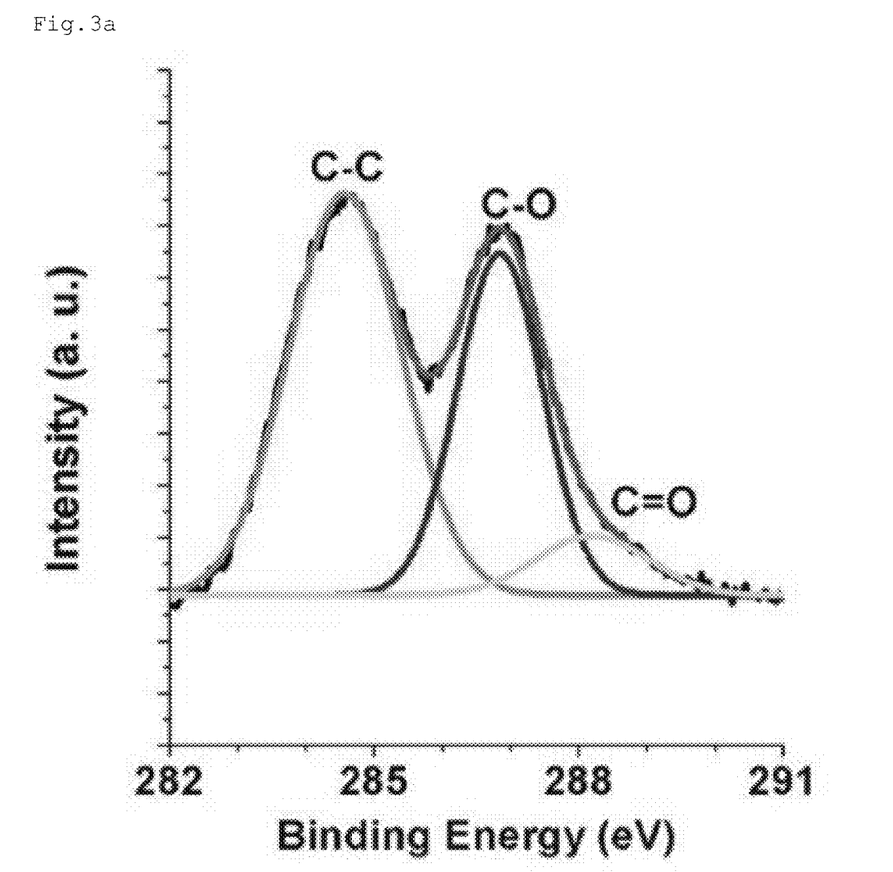
FIGS. 3a to 3f are XPS results analyzed in each step of a process for preparing a hybrid layer included in a biosensor in accordance with an example of the present disclosure.
Figure 3B:
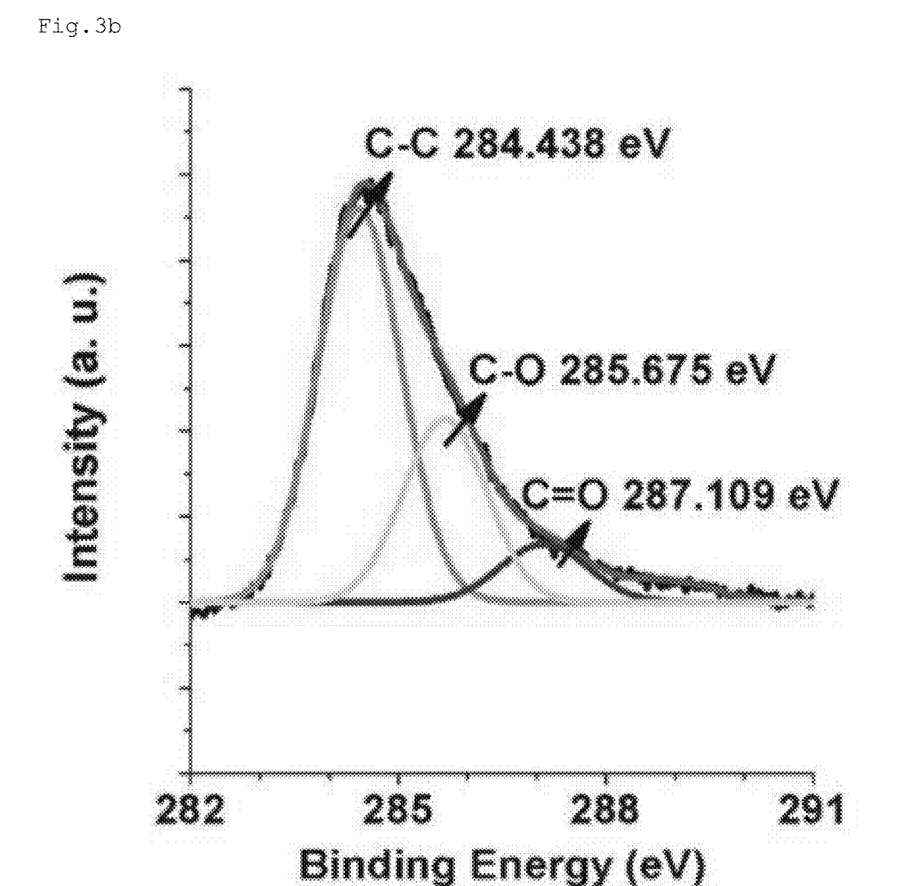
Figure 3C:
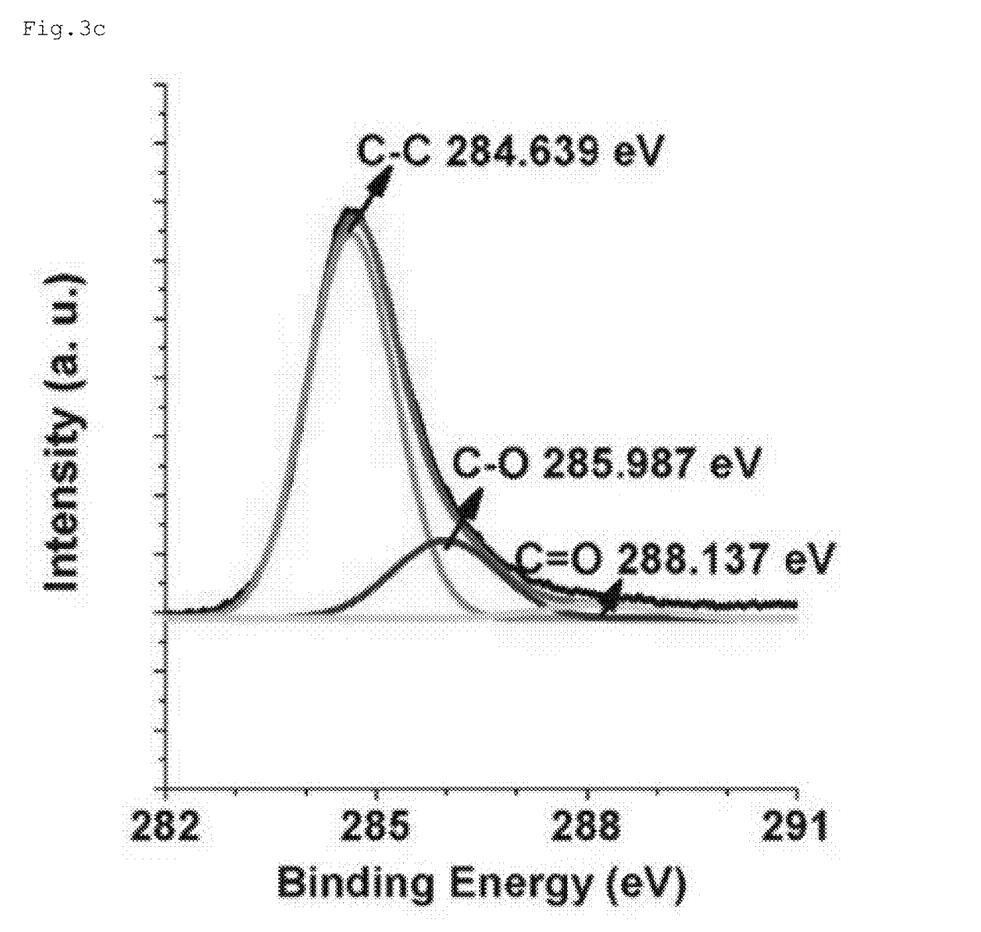
Figure 3D:
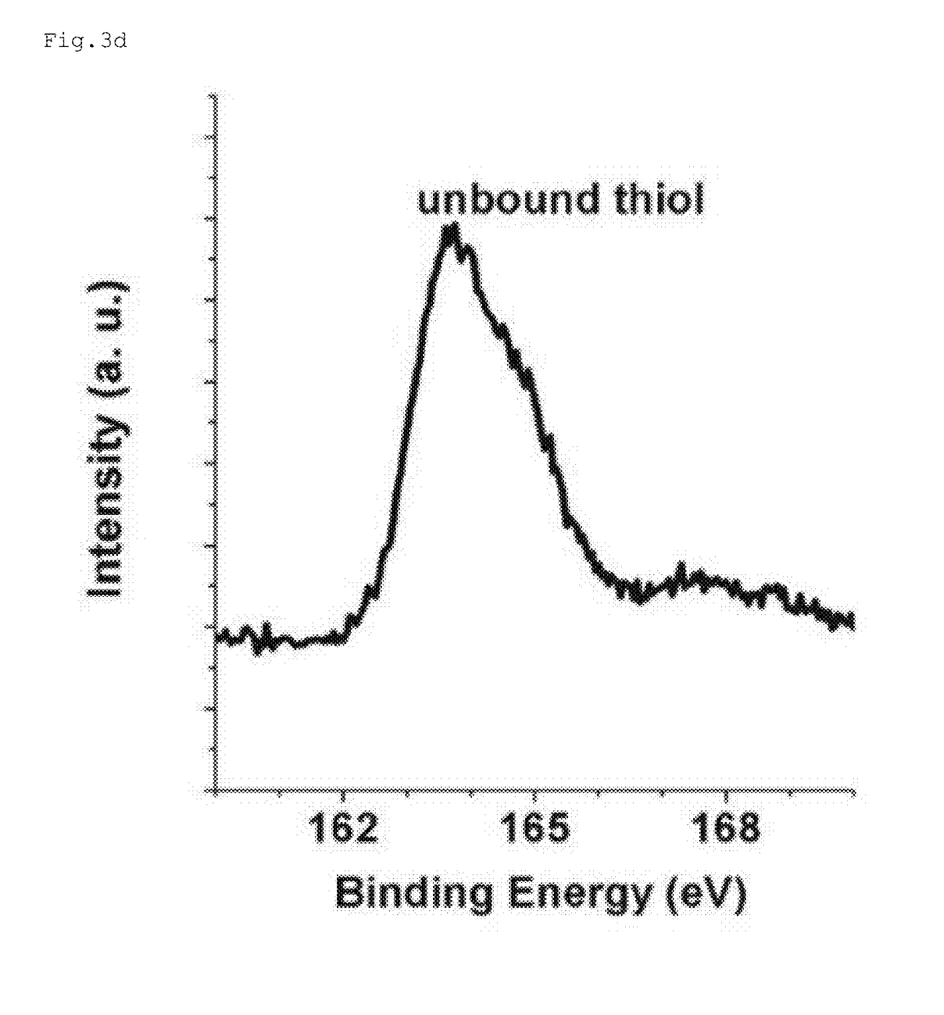
Figure 3E:
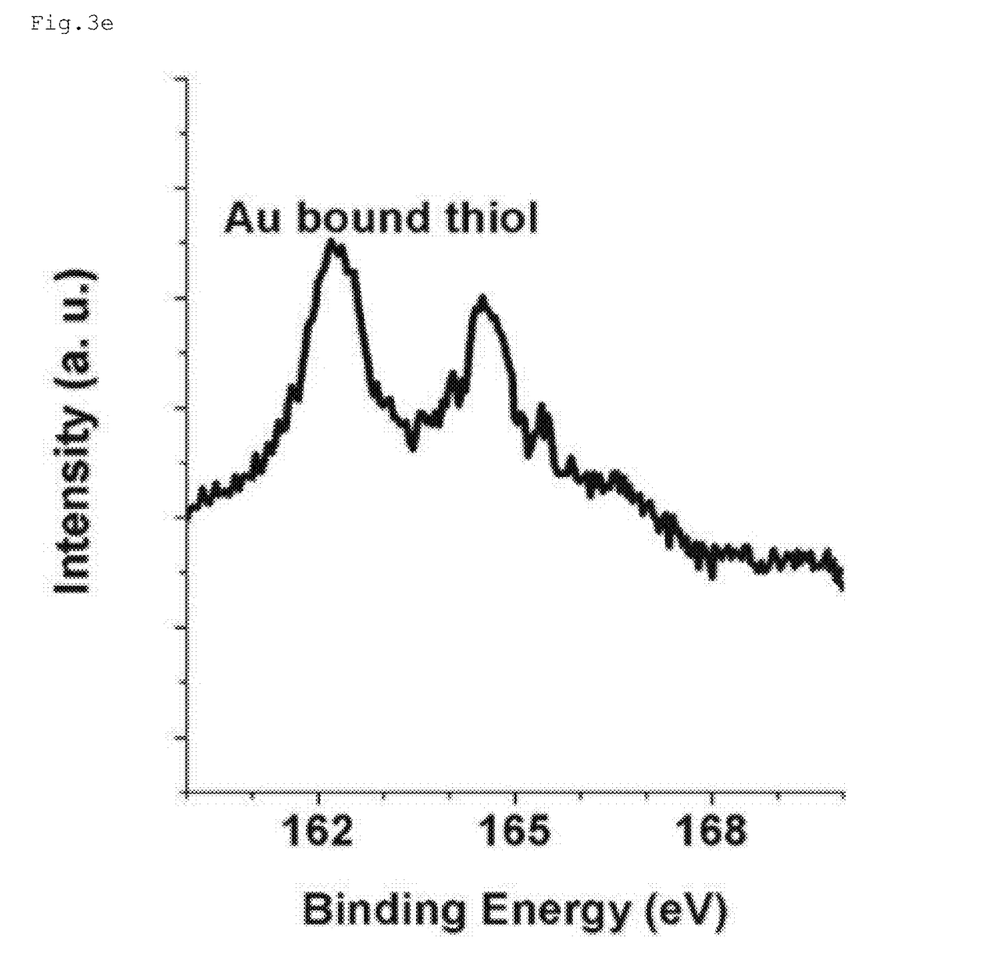
Figure 3F:
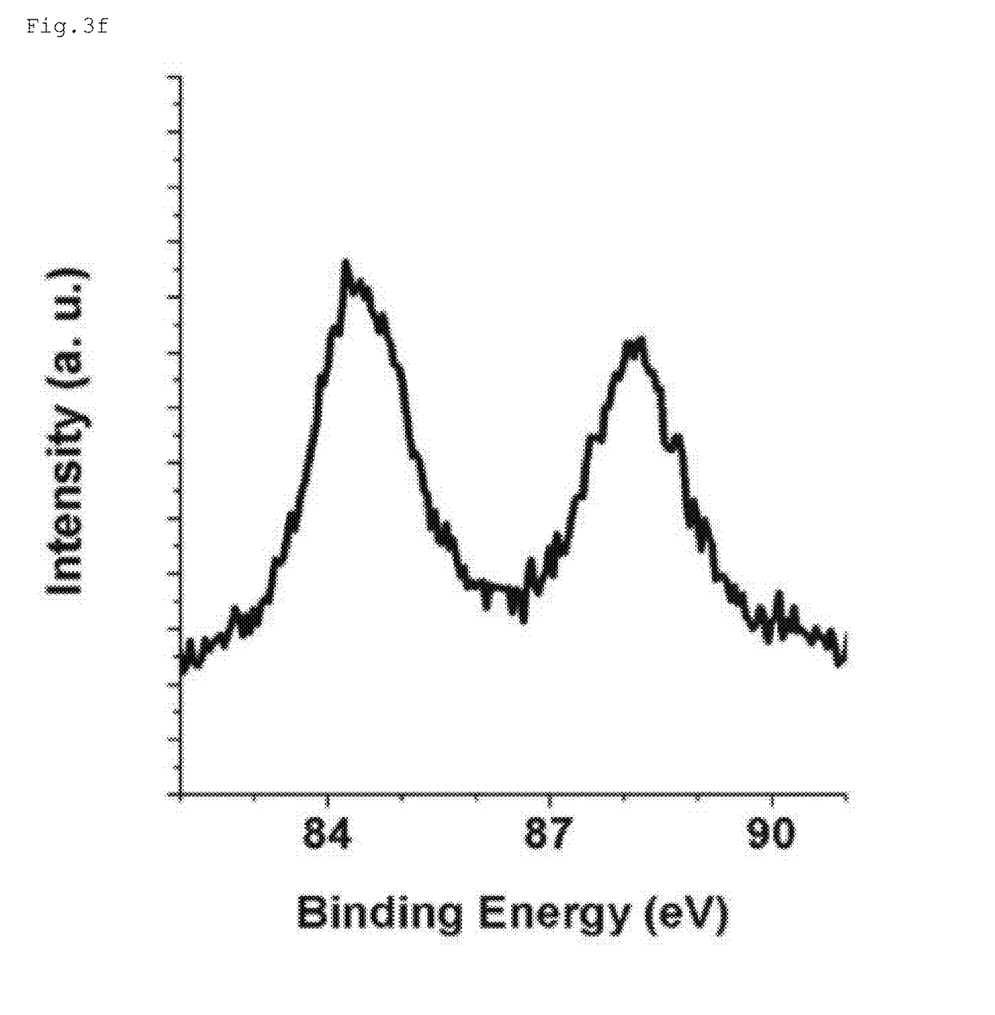

In this regard, FIGS. 3a to 3f of the present disclosure are XPS results analyzed in each step of a process for preparing an AuNP-frGO hybrid layer. To be specific, FIG. 3a shows an XPS result of a C1s region of GO, FIG. 3b shows an XPS result of a C1s region of rGO, FIG. 3c shows an XPS result of a C1s region of frGO, FIG. 3d shows an XPS result of a S2p region of frGO, FIG. 3e shows an XPS result of a S2p region of AuNP-frGO, and FIG. 3f shows an XPS result of an Au4f region of AuNP-frGO.

Figure 4:
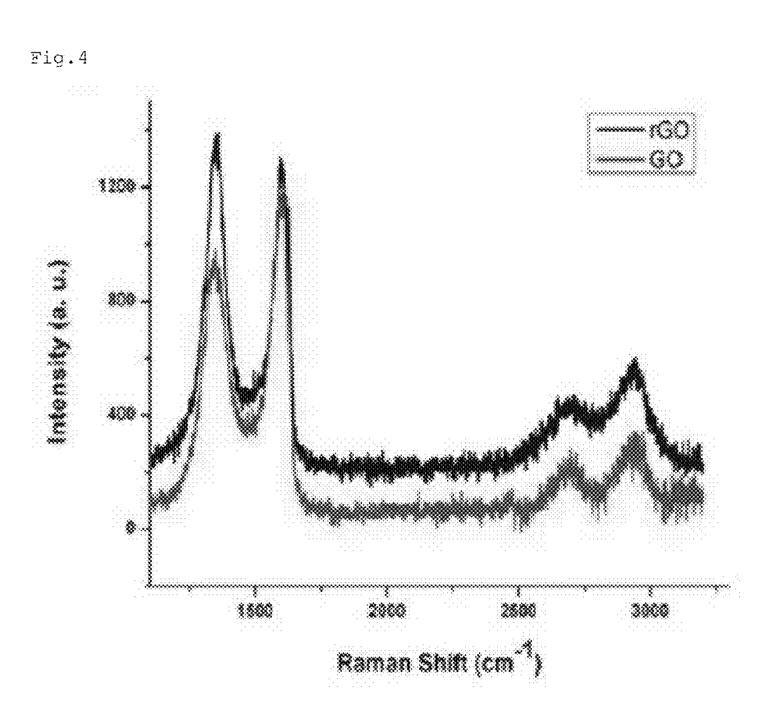
FIG. 4 is Raman spectra before and after reduction of a reduced graphene oxide layer included in a biosensor in accordance with an example of the present disclosure.

FIG. 4 of the present disclosure is Raman spectra of rGO and GO. Spectra of the rGO were marked in black, and spectra of the GO were marked in red. In both Raman spectra of the rGO and GO, a D peak was corresponded to a vibration of $sp^2$ carbon at about 1350 $cm^{-1}$, and a G peak was corresponded to a vibration of $sp^2$ carbon at about 1600 $cm^{-1}$. In case of the Raman spectra of the rGO, an intensity ratio (I(D)/I(G)) of the D and G peaks was about 1.07, which was increased significantly as compared with about 0.80 as an intensity ratio (I(D)/I(G)) of the GO. This meant that as a result of chemical reduction of GO into rGO by using hydrazine steam, some oxygen functional groups were removed, and a new bonding was resultantly created.

Figure 5A:
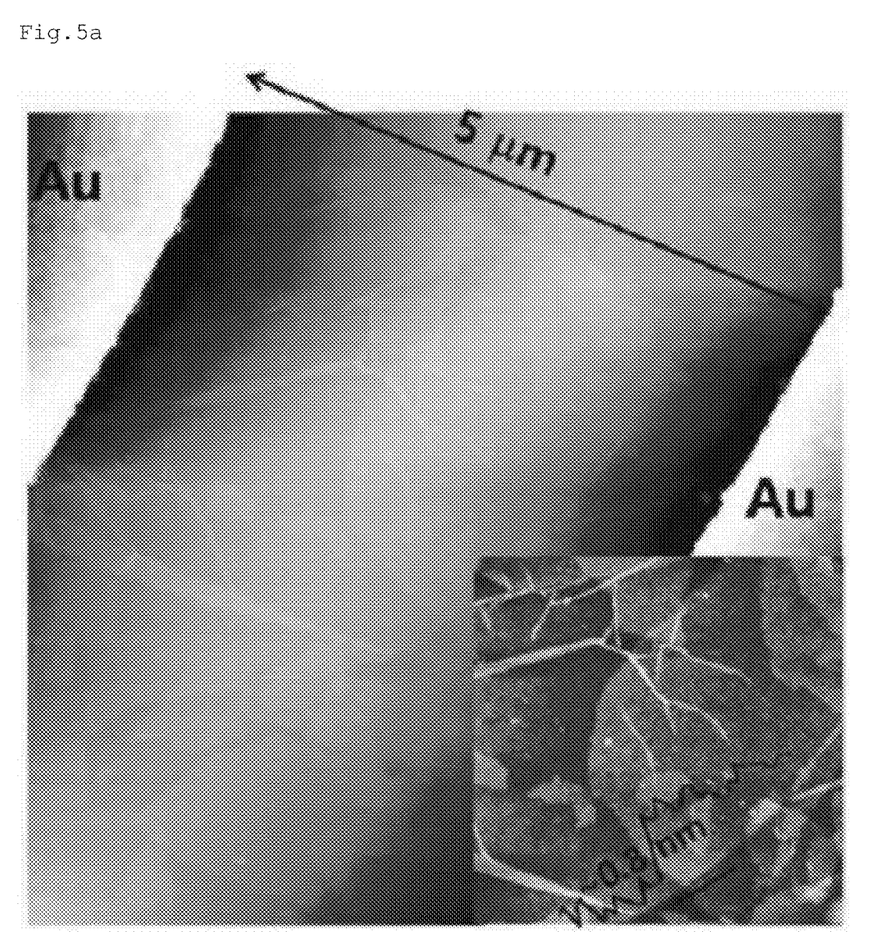
FIGS. 5a to 5c are topographical AFM images analyzed in each step of a process for preparing a hybrid layer included in a biosensor in accordance with an example of the present disclosure.
Figure 5B:
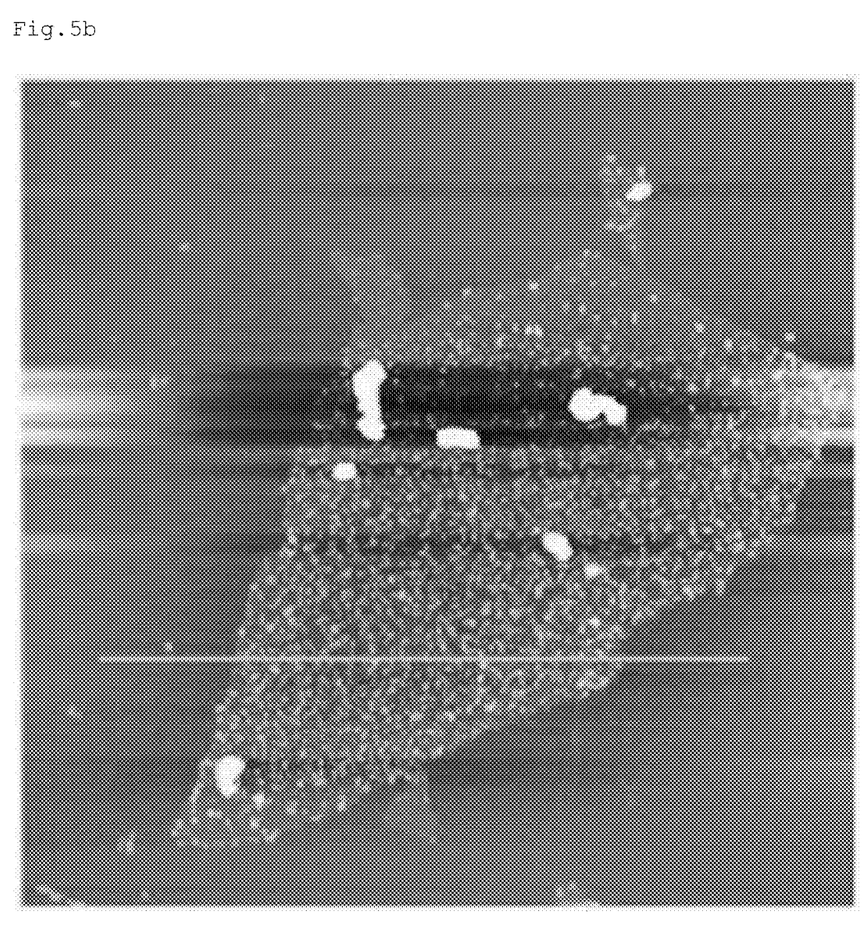
Figure 5C:
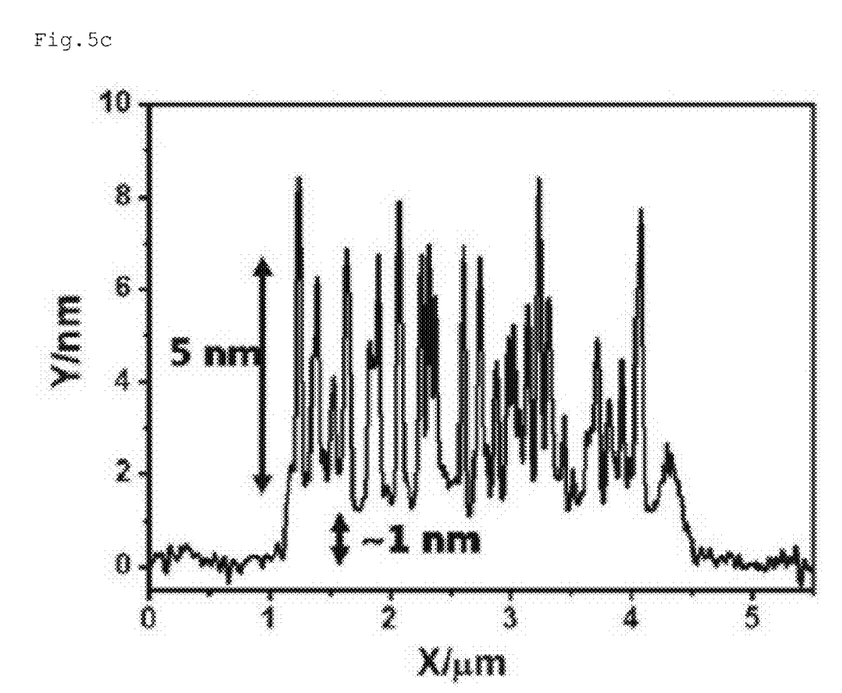

Further, FIGS. 5a to 5c of the present disclosure are topographical AFM images analyzed in each step of a process for preparing an AuNP-frGO hybrid layer. To be specific, FIG. 5a shows a topographical AFM image of rGO deposited on a $SiO_2$ substrate between an Au source electrode on the upper left side and an Au drain electrode on the lower right side, and it could be seen from FIG. 5a that the rGO formed a channel between the two Au electrodes with a gap width of about 5 μm. Further, an inset of FIG. 5a shows an image of a cross-sectional analysis of the rGO, and it could be seen from the inset that the rGO had a structure overlapped monolayer by monolayer.

Further, FIGS. 5b and 5c relate to a topographical AFM image of the AuNP-frGO hybrid layer having an area of about 7.1×7.1 $\mu m^2$. A result of AFM carried out along a white line in FIG. 5b was shown in a graph of FIG. 5c. It could be seen from FIGS. 5b and 5c that AuNP of about 5 nm was successfully immobilized on the rGO sheet by a MBDT molecular linker.

The above-described experiment analysis results shown in FIGS. 3a to 3f, FIG. 4, and FIGS. 5a to 5c were correlated with each other. Therefore, hereinafter, a sequence of a process for preparing an AuNP-frGO hybrid layer will be explained based on a correlation among the drawings.

Firstly, the drawing related to forming rGO by reducing GO will be explained as below.

First, referring to FIG. 3a and FIG. 3b, a C—O peak of FIG. 3b decreased significantly as compared with that of FIG. 3a, which indicated that reduction of GO into rGO was successfully carried out. Several small oxygen functional groups could exist in the rGO, and it could be confirmed from FIG. 3b that a C—C peak appeared as a broad shoulder peak at about 284.438 eV, and simultaneously, a C—O binding energy of about 285.675 eV and a C═O binding energy of about 287.109 eV appeared.

Referring to the inset of FIG. 5a, a thickness of an rGO monolayer was measured as about 0.8 nm from the topographical AFM image. The thickness was smaller than a thickness of a GO monolayer in a range of from about 1.0 nm to about 1.4 nm. This meant that an oxygen functional group was removed from the GO and then the rGO was formed.

In particular, an increase in the D peak of the rGO formed at 1350 $cm^{-1}$ from the Raman spectroscopy in FIG. 4 was a strong increase in the defect density, and it could be resultant of the formation of sp³ C—C bonds in the basal plane of the rGO by the defunctionalized epoxide and hydroxyl groups often chemical reduction.

Secondly, the drawing related to forming frGO by bonding a MBDT molecular linker onto rGO will be explained as below.

First, referring to FIG. 3b and FIG. 3c, it could be seen that as frGO of FIG. 3c was formed by functionalizing rGO of FIG. 3b with a MBDT molecular linker, a C—C peak was positively shifted by about 0.2 eV to about 284.639 eV. This meant that presence of new sp³ C—C bonds was owing to the bonding of the MBDT molecule to the rGO.

Referring to FIG. 3d, it could be seen that a significant amount (about 7%) of sulfur was detected. This meant that the rGO surface was successfully functionalized with a diazotized MBDT molecule to form frGO and new C—C covalent bond was created. Further, in FIG. 3d, a binding energy of S2p around 164 eV was attributed to unbound thiol group on the frGO.

Thirdly, the drawing related to forming an AuNP-frGO hybrid layer by covalently bonding AuNP onto frGO will be explained as below.

First, FIG. 3e shows an XPS analysis result in an S2p region of AuNP-frGO, and it could be seen from FIG. 3e that there was a chemical bonding between AuNP and frGO. Referring to FIG. 3d and FIG. 3e, it could be seen that a peak around 164 eV decreased and a new peak was created around 162.2 eV. The reason why the peak around 164 eV decreased was that unbound thiol groups decreased while the AuNP was immobilized. The reason why the new peak was created around 162.2 eV was that an S2p binding energy was generated due to a bonding between a thiol group and the AuNP. In other words, it could be seen from a graph of FIG. 3e that AuNP-frGO was successfully formed.

FIG. 3f shows an XPS analysis result in an Au4f region of AuNP-frGO. In FIG. 3f, Au4f peaks were observed at both about 84.4 eV and about 88.4 eV. This meant that frGO was successfully bonded to AuNP by a MBDT molecular linker.

Further, referring to topographical AFM images of FIGS. 5b and 5c, it could be seen that AuNP was well bonded and attached to frGO. To be specific, referring to FIG. 5c, it could be seen that AuNP of about 5 nm was formed on an frGO sheet of about 1 nm.

Figure 6:
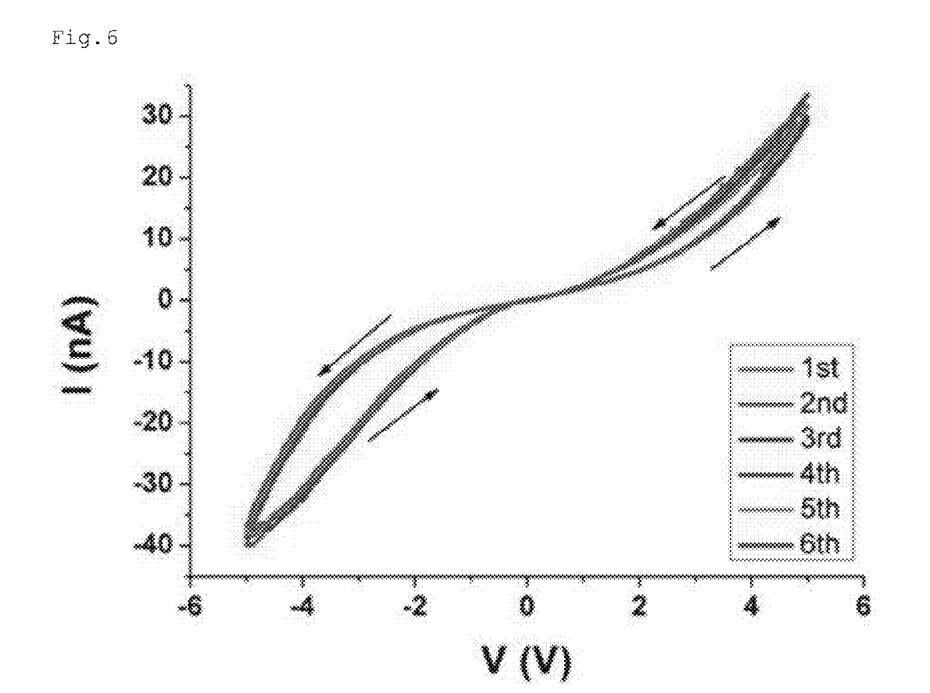
FIG. 6 is a graph of I-V characteristics of a horizontal biosensor in accordance with an example of the present disclosure.

In the present example, in order to properties of an AuNP-frGO hybrid layer included in each of the horizontal biosensor, a graph of I-V characteristics was used in addition to XPS, Raman spectrum, and AFM. FIG. 6 shows the graph of I-V characteristics. To be specific, FIG. 6 shows a linear graph of I-V characteristics of a horizontal biosensor prepared in accordance with the present example. It has been known that a graph of I-V characteristics of a device can be used to find an appropriate use of the device.

FIG. 6 of the present disclosure shows a consistently reproducible and clearly nonlinear hysteresis loop, which will be explained in detail as below.

In order to obtain the graph of I-V characteristics shown in FIG. 6, the horizontal biosensor was tested in a vacuum of about $10^4$ Torr. To be specific, the graph of I-V characteristics of the horizontal biosensor as shown in FIG. 6 was obtained by scanning applied voltages from about 0 V to about −5 V, and from about −5 V to about +5 V, and back to about 0 V in a cycle. Herein, a scanning rate was about 9.6 s/V, and a current error was in a range of from about −5 nA to about +5 nA.

Referring to FIG. 6, it could be seen that the stable hysteresis loop was sustained during continuous voltage sweeps. In order to compare with FIG. 6, experiments using a blank device that did not include AuNP and another blank device that only included AuNP without a MBDT molecular linker prepared by directly immersing rGO in an Au colloid solution were carried out, but no hysteresis loop appeared in a graph of I-V characteristics of each blank device. As a result, by comparison with experiment results of the blank devices, it could be seen that a current hysteresis loop of the graph of I-V characteristics in FIG. 6 originated from AuNP covalently bonded to frGO.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

Description of Marks of the Drawings
10: Substrate
12: Source electrode
14: Drain electrode
20: Reduced grapheme oxide layer
30: Molecular linker
40: Gold nanoparticle layer
50: Horizontal biosensor
60: Hybrid layer

What is claimed is:
1. A horizontal biosensor, comprising:
a reduced graphene oxide layer formed on a substrate;
a molecular linker formed on the reduced graphene oxide layer; and
a metal nanoparticle layer formed on the molecular linker.
2. The horizontal biosensor of claim 1, wherein the reduced graphene oxide layer is a thin layer including at least one layer, and thus has a semiconducting property.
3. The horizontal biosensor of claim 1, wherein the molecular linker includes a diazonium group at its first end, and a thiol group, a hydroxyl group, or an amine group at its second end.
4. The horizontal biosensor of claim 3, wherein the diazonium group is immobilized on the reduced graphene oxide layer by using a self-assembly function.
5. The horizontal biosensor of claim 3, wherein the thiol group, the hydroxyl group, or the amine group is covalently bonded to the metal nanoparticle layer.
6. A method for preparing a horizontal biosensor, the method comprising:
forming a reduced graphene oxide layer on a substrate;
forming a molecular linker on the reduced graphene oxide layer; and
forming a gold nanoparticle layer on the molecular linker.
7. The method of claim 6, wherein the forming a reduced graphene oxide layer includes forming a graphene oxide layer on the substrate and reducing the graphene oxide layer.

* * * * *